United States Patent [19]

Martin et al.

[11] Patent Number: 4,887,998
[45] Date of Patent: Dec. 19, 1989

[54] HYPODERMIC NEEDLE GUARD

[76] Inventors: Catherine L. Martin, 12 Sweetwater, Irvine, Calif. 92715; Brian R. Williams, 367 N. Richard St., Orange, Calif. 92669

[21] Appl. No.: 132,418

[22] Filed: Dec. 14, 1987

[51] Int. Cl.⁴ ............................................. A61M 5/00
[52] U.S. Cl. .................................. 604/110; 604/198; 604/263
[58] Field of Search ............... 604/110, 198, 192, 263, 604/187, 136

[56] References Cited

U.S. PATENT DOCUMENTS 4,664,654  5/1987  Strauss .................................. 604/198
4,702,738 10/1987  Spencer ................................ 604/198
4,790,828 12/1988  Dombrowski et al. ............. 604/198

FOREIGN PATENT DOCUMENTS 1054316  2/1954  France ............................ 604/192 X Primary Examiner—John D. Yasko
Attorney, Agent, or Firm—Price, Gess & Ubell

[57] ABSTRACT

An apparatus for preventing injury from a used hypodermic needle. Prior to withdrawal from below the skin, a spring-loaded mechanism is deployed which advances a protective sheath towards the tip of the hypodermic needle. As the needle is withdrawn the protective sheath advances beyond the tip of the needle where a positive locking mechanism positively and irreversibly encapsulates the tip of the needle.

15 Claims, 4 Drawing Sheets

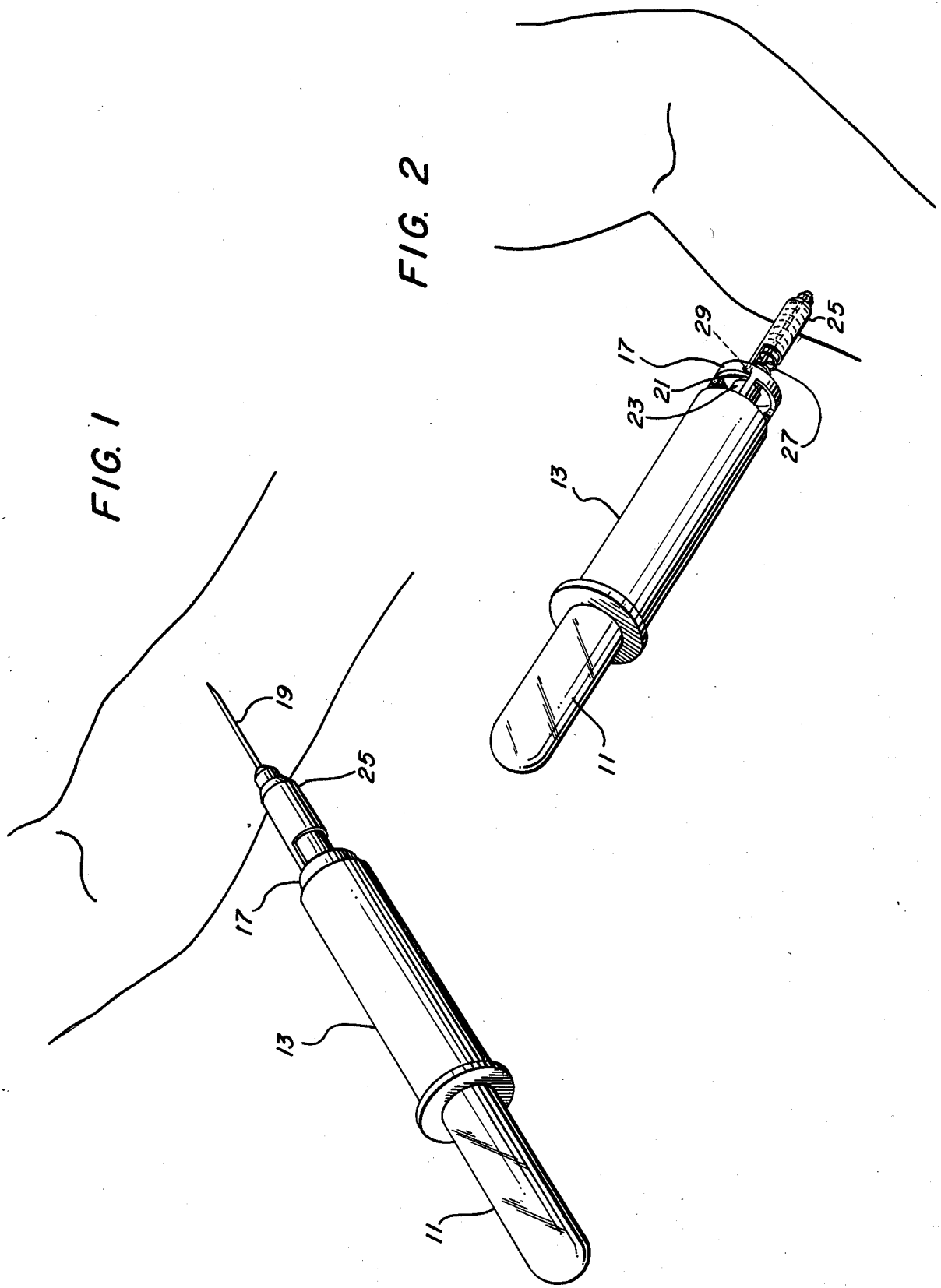

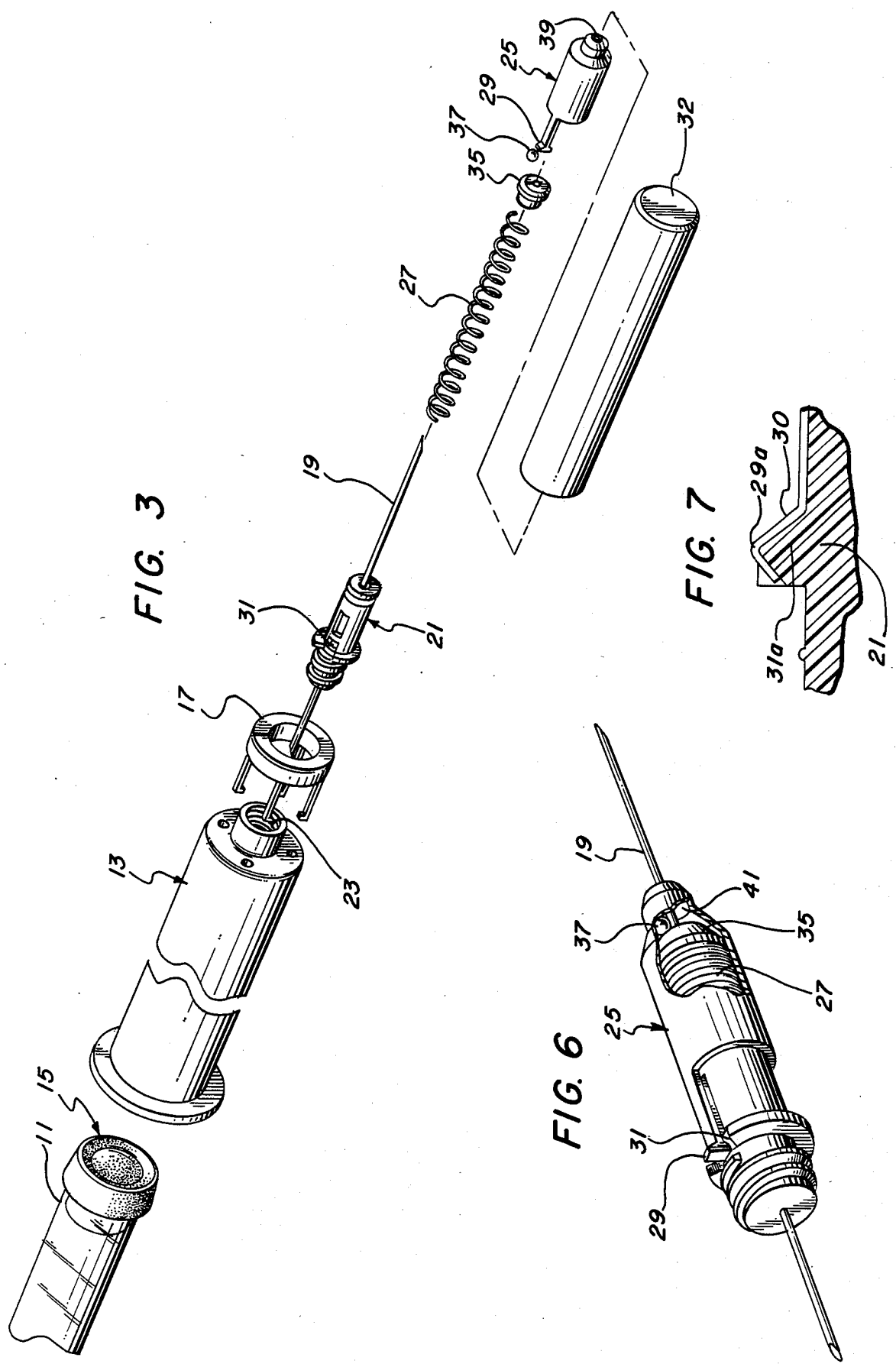

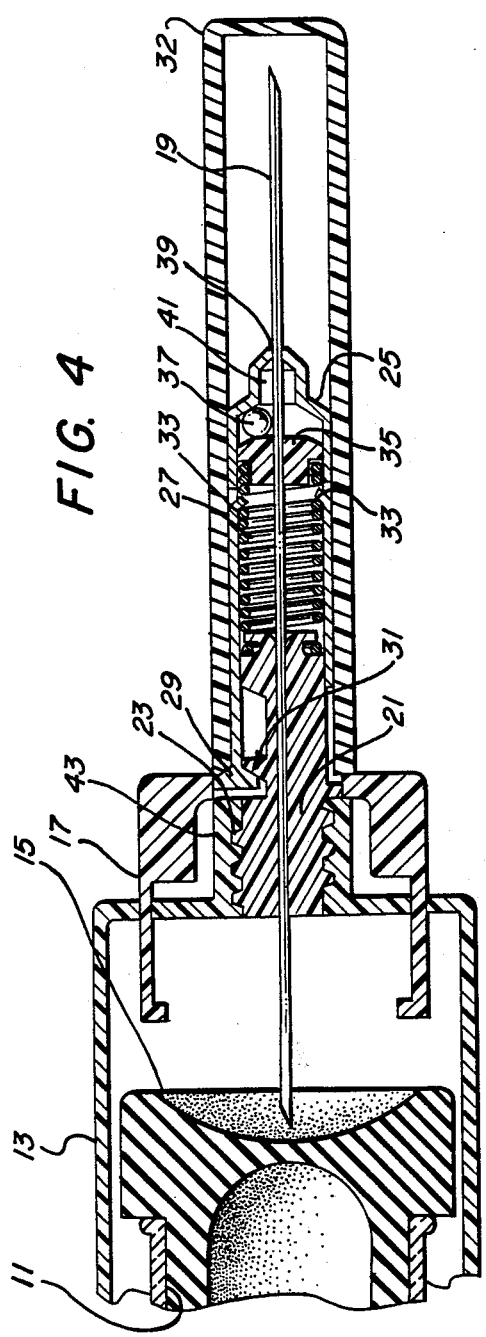
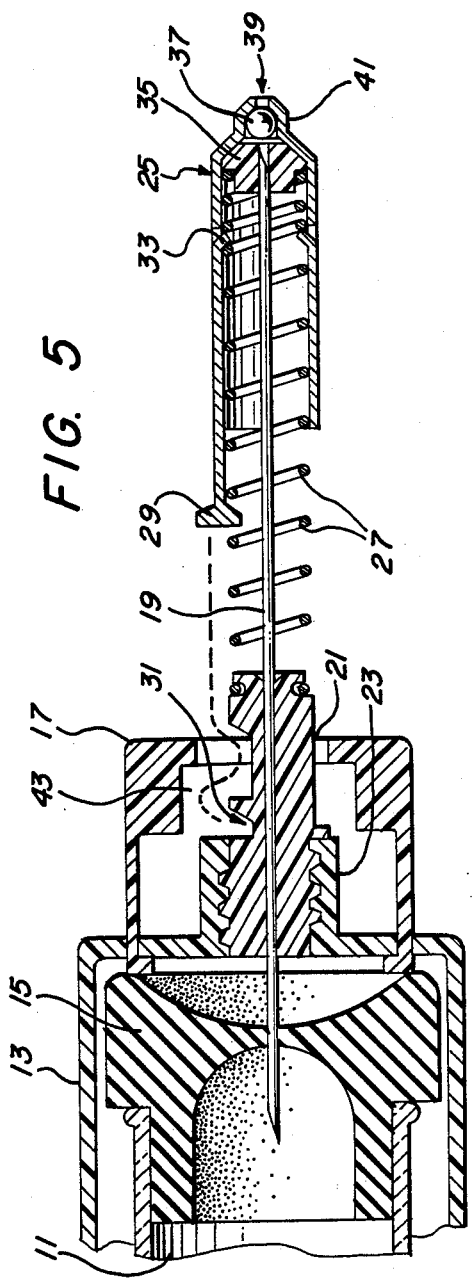

HYPODERMIC NEEDLE GUARD

BACKGROUND OF THE INVENTION

1. Field of the Invention

Hypodermic needles are commonly used to both inject substances into and extract substances out of human and animal bodies. Such hypodermic needles are typically disposable and are discarded after one use. The problem presented by the disposal of a hypodermic needle, and indeed, any handling of the hypodermic needle after its use, is the potential for being injured by the sharp end of the needle. This is particularly dangerous because following the perforation of a patient's skin, the needle may be contaminated and therefore capable of spreading diseases, such as hepatitis and AIDS.

2. Description of Related Art

A number of devices have been described that provide for some form of protective shield about the tip of a hypodermic needle, see, for example, the following:

Bastien, U.S. Pat. No. 2,571,653
Adams, U.S. Pat. No. 2,847,995
Armao, U.S. Pat. No. 3,134,380
Bloch, U.S. Pat. No. 3,354,881
Alvarez, U.S. Pat. No. 4,139,009
Wickham, U.S. Pat. No. 4,237,882
Kling, U.S. Pat. No. 4,373,526 and
Larson, U.S. Pat. No. 4,639,249

The disadvantage inherent in the above devices is that none provide positive protection. In each case, a used hypodermic needle could conceivably still perforate a subsequent handler's skin. While the devices described by McFarlane in U.S. Pat. No. 4,500,312 and 4,573,981 do provide positive protection once in place, considerable risk of perforation is presented in replacing the sheath. The devices described by Leeson et al., U.S. Pat. No. 3,890,971; Sampson, U.S. Pat. No. 4,573,976 and Mitchell, U.S. Pat. No. 4,631,057, are affixed to a syringe and, subsequent to an injection, can be extended beyond the exposed needle and locked into position. The disadvantage inherent in these designs is that a non-automatic deliberate movement is required to slide the guard in place. This leaves the needle tip exposed for a period of time. Furthermore, the needle tip is merely retracted and not actually encapsulated, and finally, these devices envelope the entire syringe and are therefore of considerable size and cost. Such a configuration precludes such a design's use in conjunction with a multi-draw blood drawing device. Recently ICU Medical, Inc. introduced a product called "High Risk Needle," which has a similar disadvantage in that a deliberate movement is required after its use leaving the needle tip exposed for a period of time.

SUMMARY OF THE INVENTION

It is an object of this invention to provide a hypodermic needle guard which is automatically deployed to shield the tip of the hypodermic needle at the time of withdrawal from below the skin so that the needle tip is not exposed subsequent to use. It is also an object of the present invention that the needle guard provide positive protection by providing an impenetrable encapsulation of the needle tip. It is a further object of the present invention to make this device as small and unobtrusive as possible.

In the preferred embodiment of the present invention, a protective sheath is slidably affixed about the hypodermic needle. A spring, once released via a trigger mechanism, causes the forward most portion of the protective sheath to advance to just beyond the tip of the needle. This position allows a ball to be forced into the path of the needle thereby preventing its re-emergence from within the protective sheath. The protective sheath can be deployed by release of the spring while the needle tip is still under a patient's skin. As the needle is withdrawn, the spring pushes the sheath to just beyond the tip of the needle where it is inextricably and impenetrably encapsulated. As the entire device attaches about the hypodermic needle only and does not encompass the syringe portion, it is very small in size and bulk.

BRIEF DESCRIPTION OF THE DRAWINGS

Other objects and many of the attendant advantages of this invention will be readily appreciated as the same becomes better understood by reference to the following detailed description when considered in conjunction with the accompanying drawings in which like reference numerals designate like parts throughout the figures thereof and wherein:

FIG. 1 is a perspective view of the device attached to a hypodermic needle in its retracted position prior to deployment;

FIG. 2 is a perspective view of the device after deployment in its extended position prior to final withdrawal of the needle from the arm;

FIG. 3 is an exploded view of the components of the hypodermic needle guard and syringe;

FIG. 4 is a sectional view of the needle guard in place and in its retracted position;

FIG. 5 is a sectional view of the device in its fully extended position;

FIG. 6 is a partially cut-away perspective view of the needle guard; and

FIG. 7 is a cross-section of a hook member in its locked position.

DESCRIPTION OF THE PREFERRED EMBODIMENTS

Figure 8:
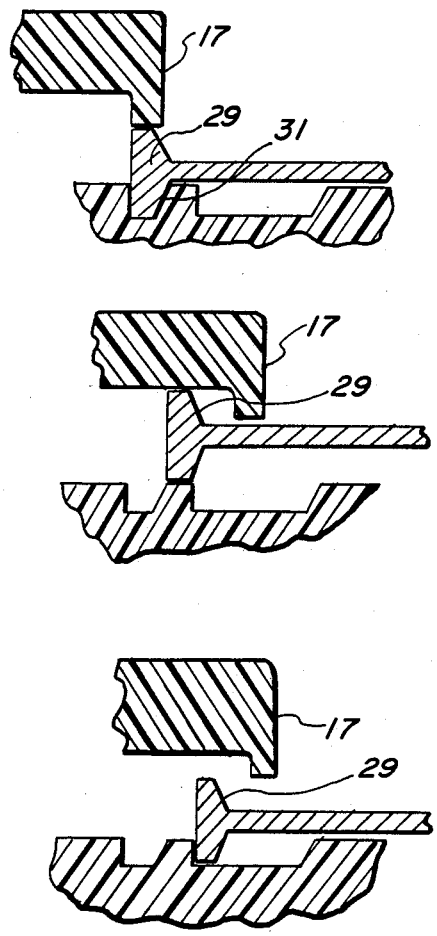
FIG. 8 illustrates the release mechanisms in sequence.

The following description is provided to enable any person skilled in the field of medical devices to make and use the present invention and sets forth the best modes contemplated by the inventor of carrying out his invention. Various modifications, however, will remain readily apparent to those skilled in the art, since generic principles of the present invention have been defined herein specifically to provide an improved hypodermic needle guard.

The device of the present invention is adaptable for combination with the hypodermic needle itself and can therefore be used in conjunction with any number of injection or extraction apparatuses.

FIG. 1 shows the device attached to the hypodermic needle in its retracted position prior to an extraction of blood. At this point, the needle is used exactly as any unguarded needle would be used. FIG. 2 shows the device in its extended position prior to withdrawal of the needle from the arm. After a blood sample is extracted but prior to withdrawal of the needle from the arm, the ampule 11 is forced to the bottom of the ampule holder 13 which causes extension of the release collar 17 as shown. This in turn allows disengagement of the hook 29 and the spring 27 forces the protective sheath 25 towards the skin. As the needle 19 is withdrawn from under the skin, the protective sheath simultaneously slides towards and just beyond the tip, at which point the ball 37 is forced into the chamber 41 effectively and irreversibly encapsulating the needle tip. The used hypodermic needle may now be handled without danger of accidental injury.

FIG. 4 shows the device of the present invention affixed to a hypodermic needle used to draw blood. The hypodermic needle 19, attached to a threaded base 21 has been screwed into an ampule holder 13 via the receiving threads 23. An evacuated ampule 11 capped by a penetrable rubber septum 15, has been partially inserted into the ampule holder 13. The protective sheath 25 is shown in its retracted position. A coil spring 27 biases the sheath towards the tip of the needle but is restrained from actually extending towards the needle tip by the hook 29 engaged over catch 31. The position of the release collar 17 prevents the hook from lifting and disengaging the catch. Prior to threading the needle base 21 onto the ampule holder 13 and hence prior to positioning the hook 29 under the release collar 17 to prevent its disengagement, the hook is held in place by the outer cap 32. This outer cap 32 insures that the needle remains sterile until its use and also prevents accidental injury. Once the needle base 21 is screwed into the ampule holder 13 and just prior to use, the outer cap 32 is pulled off. At this point, the hypodermic needle can be used in the normal manner. When the needle tip has penetrated a vein, the ampule 11 is forced further into the ampule holder 13 so that the needle pierces the rubber septum 15 and the rubber septum just engages the release collar 17. The vacuum within the ampule draws the blood sample up into the ampule. The device in its retracted position is so small and unobtrusive that it does not interfere in use of the needle.

Due to its central anchor point 33, the single spring 27 is simultaneously able to bias the protective sheath towards the needle tip and the slider member 35 towards the end of the protective sheath. Alternatively, the anchoring can be achieved by a slight crimp in the protective sheath 25 at this same location. The angled configuration of the interior of the protective sheath adjacent to the chamber of reduced diameter insures that the ball, under compression of the spring, is constantly being urged towards the center axis of the sheath regardless of the positioning or orientation of the hypodermic needle. Whether upside down or right side up, the ball is being pressed towards the center of the chamber. Only the presence of the needle 19 prevents the ball 37 from entering the smaller chamber 41, the diameter of which is approximately equal to but larger than the diameter of the ball.

Figure 9:
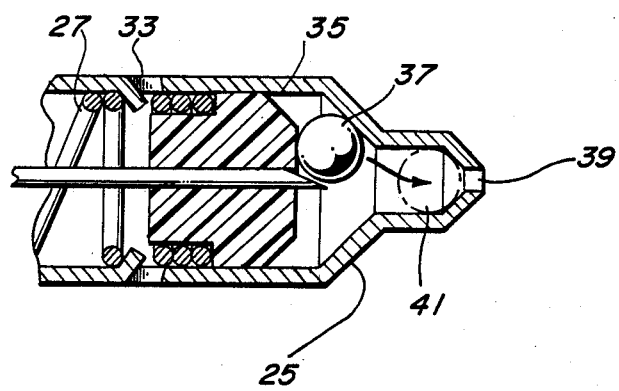
FIG. 9 illustrates a transient intermediate position of the device between its retracted and fully extended position.

FIG. 5 shows the device in its extended position wherein a positive locked protection is offered from the sharp end of the needle. When the blood drawing operation is completed, the ampule 11 is forced the remaining distance to the extreme end of the ampule holder 15. This in turn pushes the release collar 17 to a position which allows disengagement of the hook 29 from the catch 31 via movement through the recessed portion 43 of the release collar 17. FIG. 8 illustrates the movement of the hook 29 as the release collar 17 is pushed further and further outward. The hook 29 has a degree of flexibility or displaceability that allows it to contort out and around the catch 31. The spring 27 forces the protective sheath 25 to a position at which the tip of the hypodermic needle 19 no longer intrudes into the chamber 41. This allows the outer portion of the spring 27 to push the ball 37 via the slider 35 into the chamber 41 effectively blocking a re-extension of the hypodermic needle 19 through the orifice 39. FIG. 9 shows a transient position of the ball 37 as it proceeds into the chamber 41 when the protective sheath 25 is extended out beyond the needle tip. The chamber is dimensional such that the needle cannot be forced in between the ball 37 and the walls of the chamber. A 3/64" diameter ball, for example, calls for a cylindrical chamber 0.050" in diameter and 0.050" deep. As the depth of the chamber is comparable to the diameter of the ball, the possibility of the ball being forced out of the chamber by any downward force of the needle is precluded. While the ball prevents the sheath from moving back down towards the base of the needle, the spring retains the protective sheath and prevents its extension completely beyond the needle tip.

FIG. 7 shows an alternative to the hook and catch depicted in FIGS. 4 and 5. The receiving slot is raised above the needle base 21 as opposed to the recessed design depicted in FIGS. 4 and 5. Prior to engagement of the hypodermic needle 19 with the ampule holder 13, the hook 29a is held in place by the outer cap in contact with the angled portion 30 of the hook. Once engaged with the ampule holder 13, the release collar contacts the outer most portion of the hook at 29a.

FIG. 3 shows an exploded view of the parts shown in cross-section in FIG. 4 and FIG. 5, while FIG. 6 shows the parts assembled in the retracted position. It is clearly visible how the ball 37 is denied access to the chamber of reduced diameter 41 due to the presence of the needle 19. Not shown is how the outer sheath 32 would prevent the hook 29 from disengaging slot 31 and forcing the protective sheath 25 to the tip of the needle and beyond.

Obviously many modifications and variations of the present invention are possible in light of the above teachings. It is therefore to be understood that within the scope of the appended claims the invention may be practiced otherwise than as specifically described.

What is claimed is:

1. A hypodermic needle guard for preventing accidental injury after use of the hypodermic needle, comprising:
   (a) a protective sheath with an aperture slidably affixed about the hypodermic needle with the needle capable of extending through the aperture;
   (b) a biasing means for biasing the protective sheath to a position projecting just beyond the tip of the hypodermic needle;
   (c) a retaining means for releasably retaining the protective sheath near the base of the hypodermic needle;
   (d) a triggering means for releasing the retaining means, and
   (e) a locking mechanism for irreversibly locking the protective sheath about the end of the hypodermic needle when it extends beyond the tip of the needle including a non-penetrable ball member that moves in conjunction with the movement of the sheath to close the aperture.

2. The hypodermic needle guard of claim 1 wherein the retaining means comprises a slightly-flexible or displaceable projection of the protective sheath terminating in a hook, said hook engaging a catch near the base of the needle.

3. The hypodermic needle guard of claim 2 wherein the triggering means comprises a release collar slidably disposed about the base of the needle such that in a first position the hook is prevented from disengaging the catch and in a second position the hook on its slightly-flexible or displaceable stalk has enough room to move out from under the release collar whereby the triggering means can be actuated while the tip of the hypodermic needle is still below a patient's skin.

4. The hypodermic needle guard of claim 1 wherein the locking mechanism comprises the displacement of a steel ball to a captured position in front of the tip of the hypodermic needle whereby the locking mechanism provides an impenetrable encapsulation of the tip of the hypodermic needle.

5. The needle assembly of claim 1 wherein the triggering means for releasing can be deployed while the sharp point of the needle is still below a patient's skin.

6. A hypodermic needle guard for preventing accidental injury after use of a hypodermic needle, comprising:
   a sheath with an aperture slidably disposed about the needle, said sheath having sufficient rigidity to prevent needle tip penetration in normal use;
   means for extending the sheath beyond the needle tip; and
   means for closing the aperture after use of the needle including a non-penetrable ball member that can be positioned in the aperture.

7. The hypodermic needle guard of claim 6 wherein the non-penetrable member comprises a ball.

8. The hypodermic needle guard of claim 6 wherein the non-penetrable member is stored within the sheath on one side of the needle.

9. The hypodermic needle guard of claim 8 further comprising means for displacing the non-penetrable member from its stored position to a position in the aperture.

10. The hypodermic needle guard of claim 8 wherein the means for displacing the non-penetrable member comprises a spring biased slider member engaging the non-penetrable member towards a position in the aperture via a ramped configuration within the sheath.

11. The hypodermic needle guard of claim 9 further comprising means for locking the non-penetrable member in its position in the aperture.

12. A hypodermic needle guard for preventing accidental injury after use of the hypodermic needle, comprising:
   (a) a protective sheath member concentrically disposed about the hypodermic needle and slidably affixed thereto to allow movement from the base to the tip of the hypodermic needle, the interior of the sheath member defining a hollow cavity tapering to a chamber of reduced diameter and further tapering to an orifice the size of the hypodermic needle on the end facing towards the tip of the hypodermic needle;
   (b) a ball located inside the sheath member having a diameter equal to the reduced diameter of the chamber;
   (c) a slider member concentrically and slidably disposed about the hypodermic needle and located within the interior of the sheath member so as to restrict movement of the ball within the sheath member;
   (d) a first spring attached to the interior of the sheath member biasing the slider and the ball towards the chamber of reduced diameter;
   (e) a second spring disposed in between the sheath member and the base of the hypodermic needle biasing the sheath member to a position projecting just beyond the tip of the hypodermic needle;
   (f) a hook projecting from the sheath member towards the base of the hypodermic needle and engagable to a catch located near the base of the hypodermic needle to compress and retain the second spring; and
   (g) a release collar slidably disposed about the base of the hypodermic needle and positioned so as to prevent disengagement of the hook from the catch in one position while allowing disengagement when moved to a second position.

13. A hypodermic needle guard for preventing accidental injury after use of the hypodermic needle, comprising:
   (a) a protective sheath slidably affixed about the hypodermic needle;
   (b) a biasing means for biasing the protective sheath to a position projecting just beyond the tip of the hypodermic needle;
   (c) a retaining means for releasably retaining the protective sheath near the base of the hypodermic needle;
   (d) a triggering means for releasing the retaining means, and
   (e) a locking mechanism for irreversibly locking the protective sheath about the end of the hypodermic needle during normal use, wherein the locking mechanism includes the displacement of a ball member to a captured position in front of the tip of the hypodermic needle whereby the locking mechanism provides an impenetrable encapsulation of the tip of the hypodermic needle.

14. A hypodermic needle guard for preventing accidental injury after use of a hypodermic needle, comprising:
   a sheath with an aperture slidably disposed about the needle, said sheath having sufficient rigidity to prevent needle tip penetration in normal use;
   means for extending the sheath beyond the needle tip, and
   means for closing the aperture after use of the needle, including a non-penetrable ball member that can be positioned in the aperture.

15. A hypodermic needle guard for preventing accidental injury after use of a hypodermic needle, comprising:
   a sheath with an aperture slidably disposed about the needle, said sheath having sufficient rigidity to prevent needle tip penetration in normal use;
   means for extending the sheath beyond the needle tip;
   means for closing the aperture after use of the needle, including a non-penetrable member that is stored within the sheath on one side of the needle and can be positioned to close the aperture, and
   means for displacing the non-penetrable member from its stored position to a position in the aperture, including a spring biased slider member engaging the non-penetrable member towards a position in the aperture via a ramped configuration within the sheath.

* * * * *